United States Patent
Rao et al.

(10) Patent No.: US 8,852,921 B2
(45) Date of Patent: Oct. 7, 2014

(54) NON-INVASIVE SENSING OF BIOPROCESS PARAMETERS

(75) Inventors: Govind Rao, Ellicott City, MD (US); Yordan Kostov, Columbia, MD (US); Leah Tolosa, Columbia, MD (US)

(73) Assignee: University of Maryland Baltimore County, Baltimore, MD (US)

( * ) Notice: Subject to any disclaimer, the term of this patent is extended or adjusted under 35 U.S.C. 154(b) by 135 days.

(21) Appl. No.: 13/378,033

(22) PCT Filed: Jun. 21, 2010

(86) PCT No.: PCT/US2010/039337
§ 371 (c)(1),
(2), (4) Date: Feb. 15, 2012

(87) PCT Pub. No.: WO2010/148392
PCT Pub. Date: Dec. 23, 2010

(65) Prior Publication Data
US 2012/0171760 A1  Jul. 5, 2012

Related U.S. Application Data

(60) Provisional application No. 61/218,714, filed on Jun. 19, 2009.

(51) Int. Cl.
*C12M 1/00* (2006.01)
*C12M 1/34* (2006.01)
*C12M 3/00* (2006.01)
*C12M 1/24* (2006.01)

(52) U.S. Cl.
CPC ............... *C12M 23/00* (2013.01); *C12M 41/34* (2013.01); *C12M 41/00* (2013.01); *C12M 41/26* (2013.01); *C12M 23/20* (2013.01)
USPC .................. 435/288.1; 435/283.1; 435/287.1; 435/288.4; 435/288.7; 435/304.1

(58) Field of Classification Search
USPC ............................................ 435/283.1–309.4
See application file for complete search history.

(56) References Cited

U.S. PATENT DOCUMENTS

| 4,649,118 A * | 3/1987 | Anderson ................... 435/297.3 |
| 2002/0081231 A1* | 6/2002 | Shapiro et al. ............... 422/68.1 |
| 2003/0203477 A1* | 10/2003 | Hyman et al. .............. 435/289.1 |
| 2004/0062687 A1* | 4/2004 | Dordick et al. ............... 422/102 |

(Continued)

FOREIGN PATENT DOCUMENTS

| WO | WO 2004/101769 A2 | 11/2004 |
| WO | WO 2004101769 A2 * | 11/2004 |

OTHER PUBLICATIONS

Engel et al., "Multi-layer Embedment of Conductive and Non-Conductive PDMS for All-Elastomer MEMS", 2006, pp. 1-4.

(Continued)

*Primary Examiner* — Nathan Bowers
*Assistant Examiner* — Lydia Edwards
(74) *Attorney, Agent, or Firm* — Rene A. Vazquez, Esq.

(57) ABSTRACT

A system and method for measuring at least one bioprocess parameter utilizes a barrier that separates an external sensor from a culture medium. The barrier allows analytes to diffuse in and out of the culture vessel, thereby allowing the bioprocess parameter to be measured non-invasively by the external sensor.

3 Claims, 13 Drawing Sheets

(56) References Cited

U.S. PATENT DOCUMENTS

| | | | |
|---|---|---|---|
| 2005/0089993 A1* | 4/2005 | Boccazzi et al. | 435/286.2 |
| 2005/0215872 A1* | 9/2005 | Berner et al. | 600/347 |
| 2006/0099705 A1* | 5/2006 | Wikswo et al. | 435/288.5 |
| 2006/0199260 A1* | 9/2006 | Zhang et al. | 435/293.1 |
| 2007/0280984 A1* | 12/2007 | Carturan et al. | 424/422 |
| 2008/0032380 A1* | 2/2008 | Kleis et al. | 435/243 |
| 2008/0283469 A1* | 11/2008 | Pollock | 210/608 |
| 2009/0019434 A1* | 1/2009 | Gosain | 717/174 |

OTHER PUBLICATIONS

Chang-Yen et al., Am integrated optical oxygen sensor fabricated using rapid-prototyping techniques. Lab on a Chip, 2003, 3:297-301, p. 297, abstract, p. 300.

Written Opinion of the International Searching Authority for PCT/US 10/39337, filed Jun. 21, 2010, mailed Nov. 23, 2010.

International Search Report for PCT/US 10/39337, filed Jun. 21, 2010, mailed Nov. 23, 2010.

* cited by examiner

NON-INVASIVE SENSING OF BIOPROCESS PARAMETERS

This application claims priority to U.S. Provisional Application Ser. No. 61/218,714, filed Jun. 19, 2009, whose entire disclosure is incorporated herein by reference.

BACKGROUND OF THE INVENTION

1. Field of the Invention

The present invention relates to sensing of bioprocess parameters and, more particularly, non-invasive sensing of bioprocess parameters.

2. Background of the Related Art

Bioprocesses are important in a wide variety of industries such as pharmaceutical, food, ecology and water treatment, as well as to ventures such as the human genome project (Arroyo, M. et al., *Biotechnol. Prog.* 16: 368-371 (2000); Bakoyianis, V. and Koutinas, A. A., *Biotechnol. Bioeng.* 49: 197-203 (1996); Bylund, F. et al., *Biotechnol. Bioeng.* 69: 119-128 (2000); Handa-Corrigan, A. et al., *J. Chem. Technol. Biotechnol.* 71: 51-56 (1998); López-López, A. et al., *Biotechnol. Bioeng.* 63: 79-86 (1999); McIntyre, J. J. et al., *Biotechnol. Bioeng.* 62: 576-582 (1999); Pressman, J. G. et al., *Biotechnol. Bioeng.* 62: 681-692 (1999); Yang, J.-D. et al., *Biotechnol. Bioeng.* 69: 74-82 (2000)).

Most cell cultures are conducted by introducing cells and growth media in some form of sterile plastic container in an incubator. It is desirable to monitor growth parameters of the culture, such as oxygen, pH, pCO2, glucose, ions, etc. Ideally, the measurement should be as non-invasive and contamination free as possible. In this regard, related art non-invasive sensors consist of sterilizable patches that are introduced into the vessel and monitored optically from outside the vessel. These have been extensively described in the literature (V. Vojinovic et al., *Sensors and Actuators B* 114:1083-1091 (2006); T. Scheper et al., *Analytica Chimica Acta* 400: 121-134 (1999); V. Vojinovic et al., CI & CEP 13: 1-15 (2007); S. Bambot et al., *Biotechnology and Bioengineering* 43: 1139-1145 (1994)).

However, the need to introduce sensor patches into the vessel poses some problems. First, the system is not easy to manufacture, as the sensors must be inserted prior to vessel sterilization. This operation can lead to the need to recalibrate the sensors after sterilization. In cases where the sensors are to be introduced into pre-sterilized vessels, it is cumbersome to get the sensors to the right spot. Secondly, there is extensive validation needed as the sensor chemistries are in direct contact with the cell culture media. Furthermore, for long duration experiments, there is no easy means of checking sensor patch calibration or replacing a malfunctioning sensor.

SUMMARY OF THE INVENTION

An object of the invention is to solve at least the above problems and/or disadvantages and to provide at least the advantages described hereinafter.

Therefore, an object of the present invention is to provide a system and method for sensing bioprocess parameters in a manner that is less invasive than current techniques.

Another object of the present invention is to provide a system and method that senses bioprocess parameters without placing sensors inside the culture vessel.

To achieve at least the above objects, in whole or in part, there is provided a system for measuring at least one bioprocess parameter, comprising a culture vessel for containing a culture medium, wherein at least one portion of the culture vessel wall comprises a barrier membrane that is at least partially permeable to at least one predetermined analyte and a sensor mounted adjacent to the barrier membrane such that the at least one predetermined analyte that passes through the barrier membrane comes in contact with the sensor, wherein the sensor is adapted to chemically interact with the at least one predetermined analyte or to physically react to the at least one bioprocess parameter.

To achieve at least the above objects, in whole or in part, there is also provided a system for measuring at least one bioprocess parameter, comprising a culture vessel for containing a culture medium, wherein the culture vessel is defined by at least one culture vessel wall, a recess formed in a portion of the culture vessel wall such that the thickness of the culture vessel wall in the recessed area is sufficiently thin so as to be at least partially permeable to at least one predetermined analyte and a sensor positioned in the recess such that the at least one predetermined analyte that passes through the culture vessel wall in the recessed area comes in contact with the sensor.

To achieve at least the above objects, in whole or in part, there is also provided a plug-in sensor system for measuring at least one bioprocess parameter, comprising a gas impermeable optically transparent layer, a sensor positioned on the optically transparent layer adapted to interact with at least one analyte and a hydrogel layer positioned on the sensor, wherein the gas impermeable optically transparent layer, sensor and hydrogel layer together define a cartridge that is adapted to be selectively inserted into and removed from an opening in a culture vessel wall.

To achieve at least the above objects, in whole or in part, there is also provided a system for measuring at least one bioprocess parameter, comprising a culture vessel for containing a culture medium, wherein the culture vessel is defined by at least one culture vessel wall, at least two separate recesses formed in portions of the culture vessel wall such that the thickness of the culture vessel wall in the recessed areas is sufficiently thin so as to be at least partially permeable to at least one predetermined analyte and a sensor positioned in each recess such that the at least one predetermined analyte that passes through the culture vessel wall in the recessed areas comes in contact with the sensor, wherein the sensor is adapted to react to the at least one predetermined analyte.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

Figure 1:
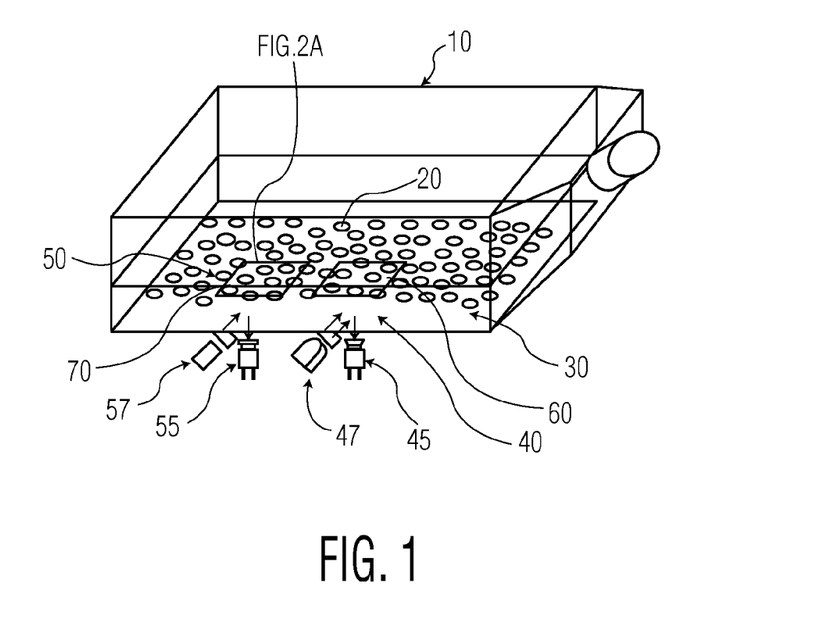
FIG. 1 is a schematic diagram of a culture vessel adapted for non-invasive sensing of bioprocess parameters, in accordance with one embodiment of the present invention.

FIG. 1 is a schematic diagram of a culture vessel adapted for non-invasive sensing of bioprocess parameters, in accordance with one embodiment of the present invention. The culture vessel 10 shown in FIG. 1 contains cells 20 and a cell culture medium 30.

Sensor patches 40/50, preferably optical chemical sensor patches, and associated excitation sources 47/57 and optical detectors 45/55 are mounted outside the culture vessel 10. Barrier membranes 60/70 provide a physical barrier between the sensor patches 40/50 and the cell culture medium 30. By way of example, barrier 60/70 may either be constructed of the same material as the vessel or of a different material. The barrier membrane is adapted to provide a sterile barrier that is at least partially permeable to the analytes that need to interact with sensor patches 40/50 in order to monitor certain bioprocess parameters.

By way of example, sensor patches 40/50 are optical sensor patches designed to measure pH and dissolved oxygen, respectively. However any other type of sensor patch known in the art for monitoring a bioprocess parameter may be used. The barrier membranes 60/70 are designed so that analytes to be measured can readily diffuse in and out of the culture vessel 10 to interact with sensor patches 40/50. Optical excitation sources 47/57 are used to optically excite the sensor patches 40/50, which then generate light emission and/or absorption that is dependent on the amount of the analytes that pass through the barrier membrane 60/70 and strike the sensor patches 40/50. The light emission and/or absorption is measured by the optical detectors 45/55.

The optical excitation source 47/57 used is matched to the type of sensor patches 40/50 used. Any combination of optical excitation sources and sensor patches known in the art may be used, depending on the bioprocess parameter being measured. Examples of optical excitation sources that can be used include, but are not limited to, light emitting diodes and laser diodes.

In one preferred embodiment, the barrier membranes 60 and 70 are suitably between 0.1 and 0.4 micron pore size, and preferably approximately 0.2 micron pore size hydrophobic membranes. Depending on the medium in which the analyte to be monitored is contained, other membranes, such as hydrophobic or oleophobic membranes, can be used. The types of membranes that can be used include ultrafiltration, dialysis, nanoporous or membranes designed for facilitated diffusion. The membranes are preferably made of synthetic or natural polymers, such as poly(ether)sulphone or cellulose derivatives. In the case of oxygen, $CO_2$ and other gaseous species, no pores may be present and the barrier material can simply be of the same material that the vessel 10 is constructed but of a thickness ranging from 0.1 to 100 microns. The culture vessel wall 80 of the non-invasive sensing system 1000a shown in FIG. 2A utilizes such a barrier material. Specifically, the barrier membrane 70 is made by forming a recess 75 into the vessel wall 80 such that this vessel wall becomes very thin (preferably between 0.1 and 100 microns) and can act as the barrier membrane 70. The sensor patch 50 is then positioned inside the recess 75 formed in the vessel wall 80. A relatively gas impermeable transparent layer 90, which can be suitably formed from polycarbonate, poly-methyl methacrylate, or using the vessel material of a thickness exceeding 1 mm, is preferably formed over the recess 75 such that the sensor patch 40 is positioned between the barrier membrane 70 and the gas impermeable transparent layer 90.

The sensor patches 40/50 can suitably be a sensing "cocktail", such as PDMS rubber that contains a gas-sensing dye. However, any type of sensing material known in the art can be used for the sensor patches 40/50. Further, although preferred pore size for measuring dissolved oxygen and pH is approximately 0.2 microns, other pore sizes may be used depending on the types of analytes being measured. Although the system shown in FIG. 1 utilizes two sensor patches 40/50 and two barrier membranes 60/70, it should be appreciated that any number of sensor patches and barrier membranes can be used.

Figure 2A:
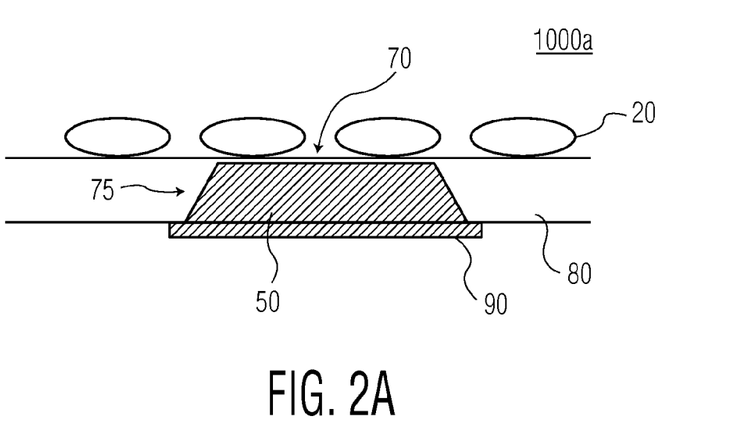
FIG. 2A is a schematic diagram of a non-invasive sensing system showing the positioning of a barrier membrane on the culture vessel wall through which analytes can diffuse, in accordance with one embodiment of the present invention; the barrier may be simply a reduced thickness of the vessel material, thereby allowing diffusible species to rapidly diffuse and contact the sensor molecule, or may be a distinct barrier material fused to the vessel.

The sensor patches 40/50 are preferably affixed to the barrier membranes 60/70 or the recess 75 using any suitable means including, but not limited to, adhesives, mechanical means (friction, size restriction or threaded), magnetic means or interdigitated means (Velcro type). Generally, any means designed to minimize mass transfer resistance and provide maximum surface contact area between the sensor patches 40/50 and the barrier membrane 60/70 is preferably used.

As will be described in more detail below, the wall 80 of the culture vessel 10 can also be modified to incorporate the barrier membranes 60/70 by drilling holes in the vessel and welding, gluing or otherwise securing the barrier membranes 60/70 across the hole. In other embodiments, these holes may be created as pores using a laser, or radiation from a nuclear decay process or by mechanical devices or molds during the vessel fabrication. A suitable barrier membrane 60/70 can then be used to seal the holes such that only analyte molecules diffuse out. The material of the vessel 10 itself may be modified in sections to make it thinner, as described above, and make it permeable with nanopore holes drilled and filled with sealing diffusible gels of poly ethylene glycol or other suitable non-toxic biocompatible material. In other embodiments, the barrier may be a dialysis membrane of selected molecular weight cutoffs. Several of these can be present on the vessel to select for ranges of analytes between 100-1000 molecular weight, between 1000-10,000, between 10,000-20,000 etc all the way up to 0.2 microns.

Figure 2B:
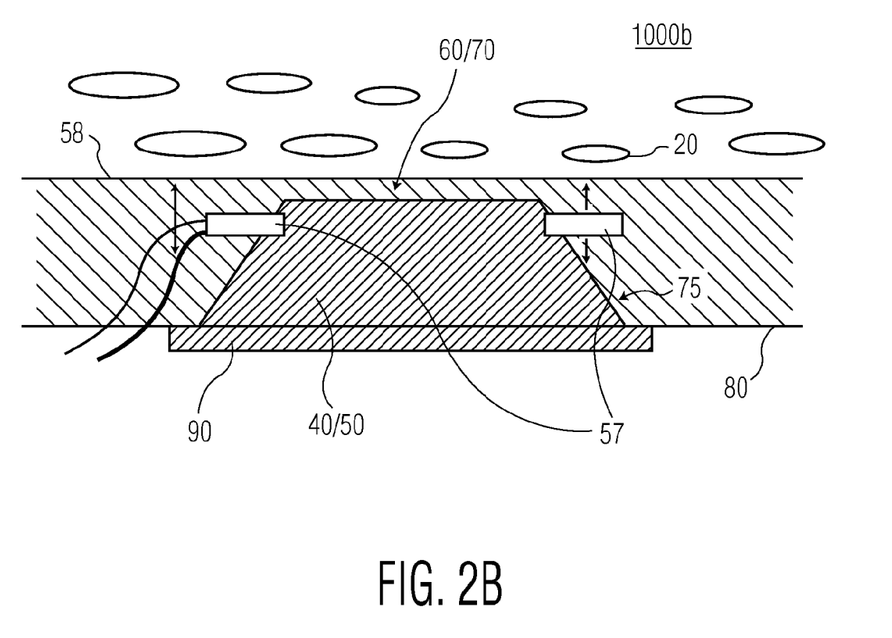
FIG. 2B is a schematic diagram of a non-invasive sensing system showing the positioning of mass transport enhancement elements for enhancing mass transport across the barrier membrane, in accordance with another embodiment of the present invention.

FIG. 2B shows a non-invasive sensing system 1000b similar to the embodiment of FIG. 2A, except that mass transport enhancement elements 57 are used to increase the mass transport across the barrier membrane 60/70 by vibrating and/or heating the sensor cocktail that make up the sensor patches 40/50. The mass transport enhancement elements 57 are suitably piezoelectric elements or heating elements, and are preferably positioned close to the barrier membrane 60/70 such that the distance between the elements 57 and the inside wall 58 of the vessel is preferably approximately the same as the thickness of the gas impermeable transparent layer 90. The mass transport enhancement elements 57 can suitably be, but are not limited to, acoustic (piezoelectric), magnetic (magnetostriction) or RF (local heating and cooling to vary the dimensions). They can be either mechanically attached to or embedded into the vessel wall 80.

Figure 2C:
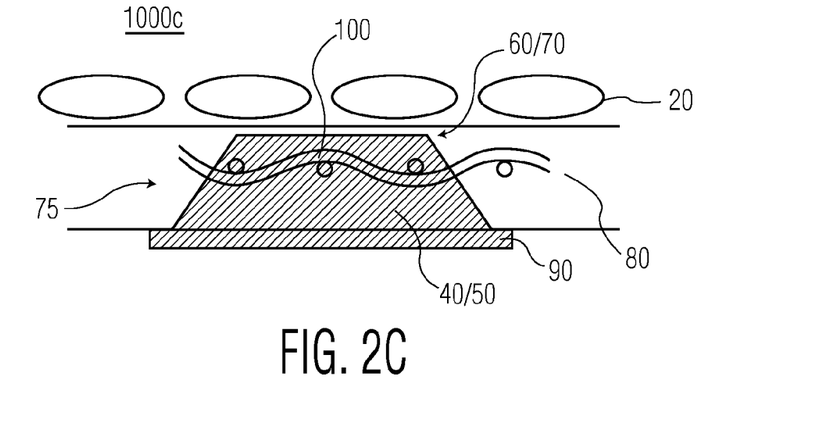
FIG. 2C is a schematic diagram of a non-invasive sensing system showing the positioning of a barrier membrane on the culture vessel wall through which analytes can diffuse, in accordance with another embodiment of the present invention.

In the embodiment of FIG. 2A, the recess 75 formed into the vessel wall 80 will weaken the vessel wall 80 at the area of the recess 75. FIG. 2C shows a non-invasive sensing system 1000c similar to the embodiment of FIG. 2A, except that a reinforcing mesh 100, preferably made of stainless steel, Teflon, or the vessel material itself is incorporated into the vessel wall 80 and extends across the recess 75. In both FIGS. 2A and 2C, the barrier function is provided by a thin layer of the vessel wall material itself.

Figure 2D:
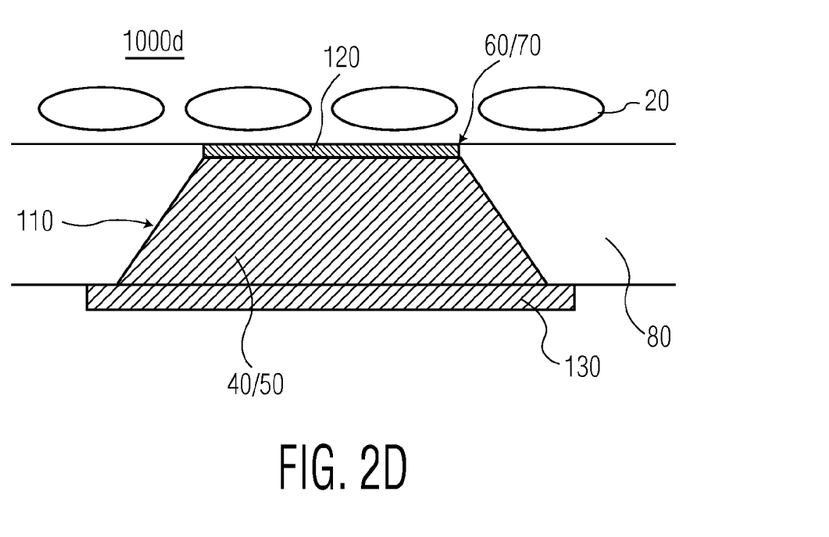
FIG. 2D is a schematic diagram of a non-invasive sensing system showing the positioning of a barrier membrane on the culture vessel wall through which analytes can diffuse, in accordance with another embodiment of the present invention.

FIG. 2D shows another non-invasive sensing system 1000d, designed for liquid cultures, in which the barrier membrane 60/70 is formed by making an opening or hole 110 in the vessel wall 80 that extends all the way through the vessel wall 80. The barrier membrane is 60/70 is then formed by covering the opening 110 with a non-porous membrane 120 on the interior side of the vessel wall 80. A water impermeable layer 130, which can be suitably formed from polycarbonate, poly-methyl methacrylate, or using the vessel material of a thickness exceeding 1 mm, is then formed over the opening 110 on the exterior side of the vessel wall 80 such that the sensor patch 40/50 is positioned between the barrier membrane 60/70 and the water impermeable layer 130. Layers 130 and 90 serve a similar purpose, which is to keep the sensor patches 40/50 in and not allow atmospheric gases or other molecules to diffuse into the sensor patch 40/50 from the back and interfere with the measurement from the sterile side.

Figure 2E:
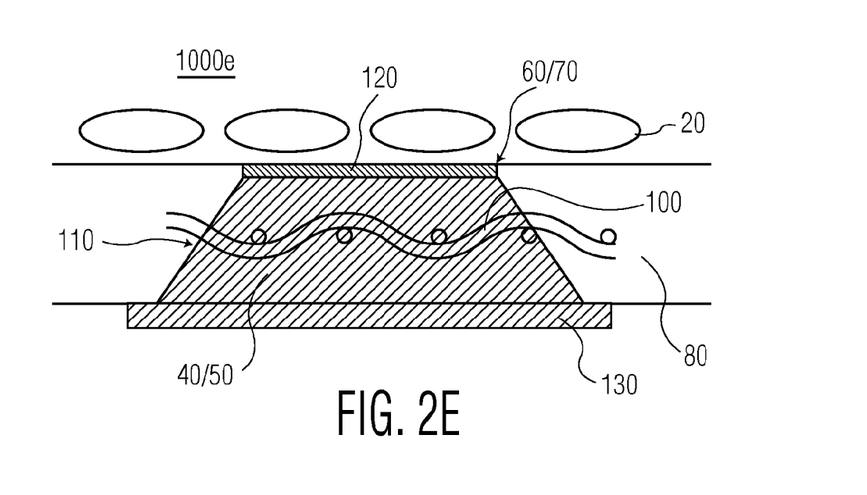
FIG. 2E is a schematic diagram of a non-invasive sensing system showing the positioning of a barrier membrane on the culture vessel wall through which analytes can diffuse, in accordance with another embodiment of the present invention.

For liquid cultures, the sensor patches 40/50 can suitably be a hydrogel with immobilized ion sensitive dye. However, any type of sensing material known in the art can be used for the sensor patches 40/50. In the embodiment shown in FIG. 2D, sensor patches 40/50 may be replaced during an experiment by removing backing 130. This allows for long duration monitoring and/or replacement of sensor patches for checking calibration without compromising sterility of the vessel and its contents. As shown in the non-invasive sensing system 1000e of FIG. 2E, a reinforcing mesh 100 can be incorporated into the vessel wall 80, such that it extends across the opening 110, in order to strengthen the vessel wall 80 at the area of the opening 110.

Figure 2F:
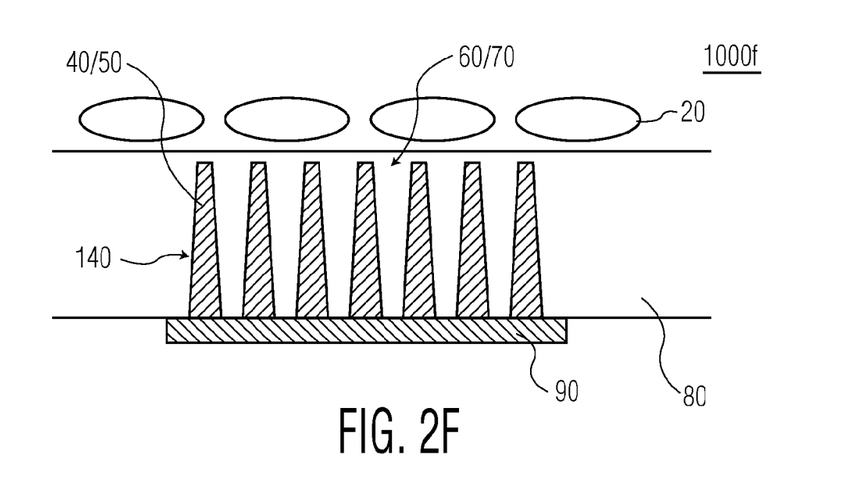
FIG. 2F is a schematic diagram of a non-invasive sensing system showing the positioning of a barrier membrane on the culture vessel wall through which analytes can diffuse, in accordance with another embodiment of the present invention.
Figure 2G:
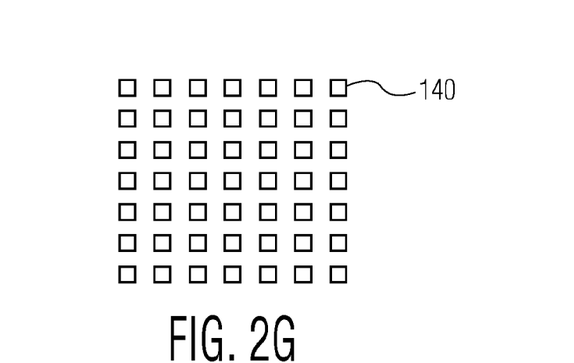
FIG. 2G is a bottom view of the embodiment of FIG. 2F.

FIG. 2F shows a non-invasive sensing system 1000f designed for gas phase measurements in which multiple small recesses 140 in a grid pattern are used instead of the large recess 75 shown in FIGS. 2A and 2C. Each small recess 140 is preferable filled with a sensing patch or "cocktail" 40/50. The multiple small recesses 140 result in stronger vessel wall 80 without having to use a reinforcing mesh. FIG. 2G shows a bottom view of the grid pattern of small recesses 140.

Figure 2H:
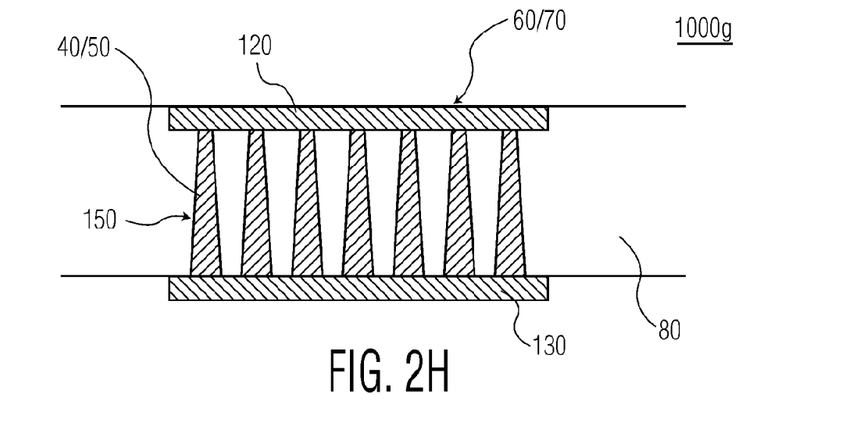
FIG. 2H is a schematic diagram of a non-invasive sensing system showing the positioning of a barrier membrane on the culture vessel wall through which analytes can diffuse, in accordance with another embodiment of the present invention.

This design can also be utilized in a non-invasive sensing system 1000g designed for liquid phase measurements, as show in FIG. 2H. This embodiment is similar to the embodiment of FIG. 2D, except that multiple small holes or openings 150 are used instead of one large opening, and sensor patches or "cocktails" 40/50 are used in each opening 150.

Figure 2I:
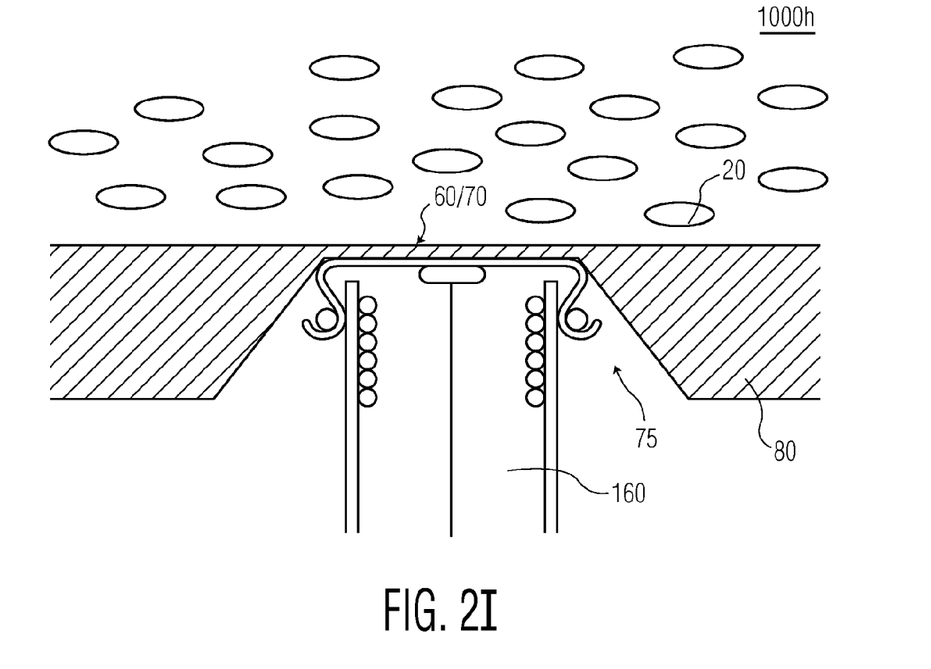
FIG. 2I is a schematic diagram of a non-invasive sensing system showing the positioning of a conventional Clark electrode in the recess of the vessel wall, in accordance with another embodiment of the present invention.

FIG. 2I shows a non-invasive sensing system 1000h that utilizes a conventional Clark electrode 160. Similar to the embodiments described above, the barrier membrane 60/70 is made by forming a recess 75 into the vessel wall 80 such that the vessel wall becomes very thin (preferably between 0.1 and 100 microns) and can act as the barrier membrane 60/70. The Clark electrode 160 is positioned within the recess 75.

Figure 2J:
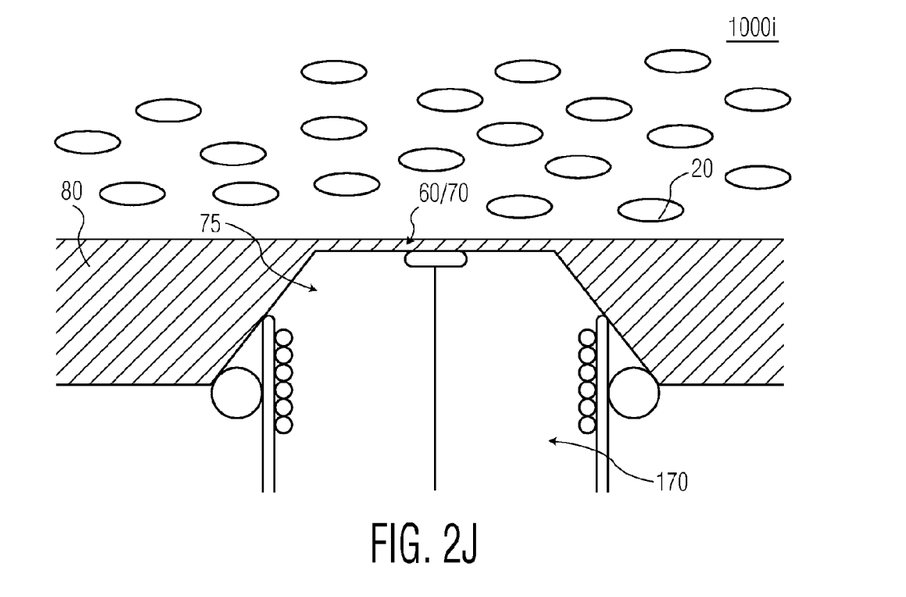
FIG. 2J is a schematic diagram of a non-invasive sensing system showing the positioning of a "naked" Clark electrode in the recess of the vessel wall, in accordance with another embodiment of the present invention.

FIG. 2J shows a non-invasive sensing system 1000i similar to the embodiment of FIG. 2I, except that a "naked" Clark electrode 170 is utilized. In this embodiment, the barrier membrane 60/70 also acts as the membrane for the Clark electrode 170.

Figure 2K:
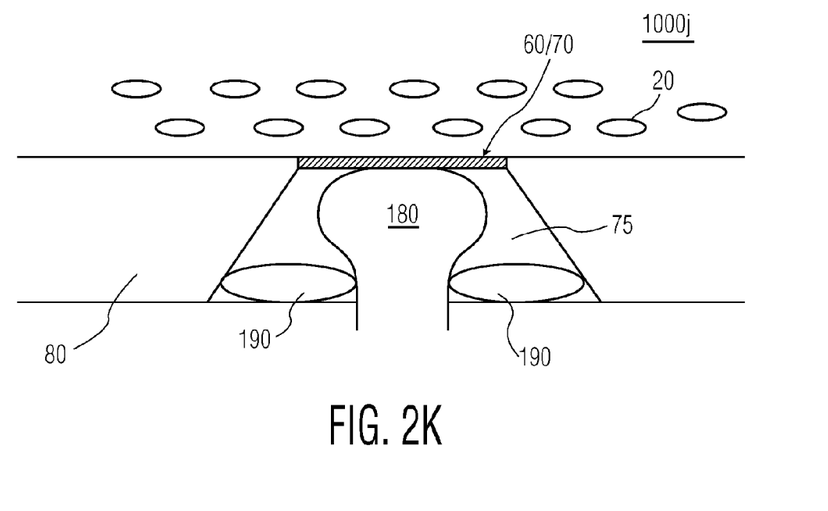
FIG. 2K is a schematic diagram of a non-invasive sensing system showing the positioning of a pH electrode in the recess of the vessel wall, in accordance with another embodiment of the present invention.

FIG. 2K shows a non-invasive sensing system 1000*j* that utilizes a pH electrode 180 positioned within the recess 75. An O-Ring 190 is used to seal off the recess 75.

Figure 3:
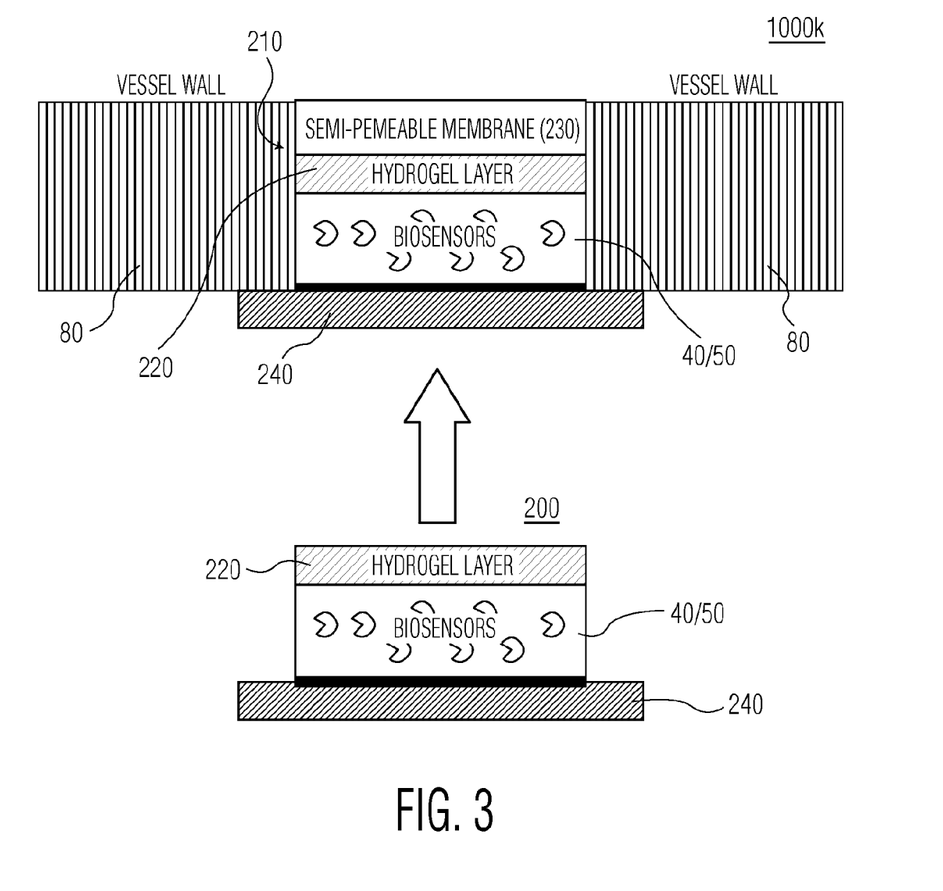
FIG. 3 is a schematic diagram of a non-invasive sensing system utilizing a plug-in sensor cartridge, in accordance with another embodiment of the present invention

FIG. 3 shows a non-invasive sensing system 1000*k* that utilizes a plug-in sensor cartridge 200. The plug-in sensor cartridge 200 fits into an opening 210 in the vessel wall 80, and can be inserted and removed as needed. The biosensors for measuring glucose, glutamine, etc. are preferably immobilized or suspended in a hydrogel layer or are in buffer solution.

In the embodiment of FIG. 3, the sensor cocktail 40/50 is made up of biosensors in a buffer solution. The sensor cocktail 40/50 is prevented from leaking by a hydrogel layer 220. The plug-in sensor cartridge 200 is inserted into a cavity 210 in the reactor vessel wall 80. If the hydrogel layer 220 does not provide sufficient sealing, an optional semi-permeable membrane 230 may be used on top of the hydrogel layer 220. The semi-permeable membrane 230 allows for the free diffusion of small molecules (glucose, glutamine, etc.) to come in contact with the biosensors in the sensor cocktail 40/50. The concentration of the nutrient is determined by the rate at which a signal plateau is reached. A gas impermeable transparent layer 240 is attached so as to form an outside wall or cap of the cartridge 200.

The semi-permeable membrane 230 and hydrogel layer 220 together are preferably between 0.1 microns and 10 microns thick to provide minimal diffusional resistance. The sensor cocktail 40/50 is suitably approximately 1 mm thick, although other thicknesses can be used.

Figure 4:
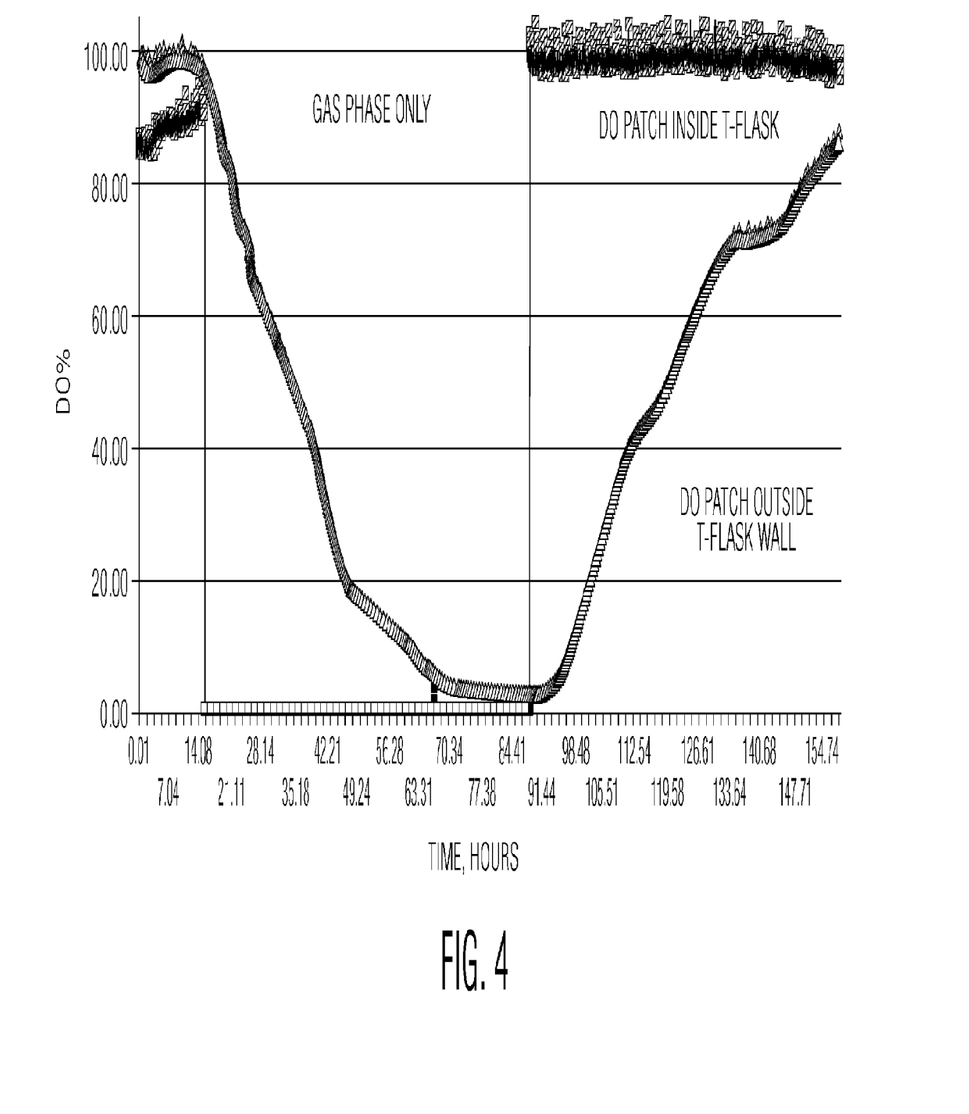
FIG. 4 is a plot comparing the outputs, for gas phase measurements, of a dissolved oxygen sensor positioned inside a culture vessel and a dissolved oxygen sensor positioned outside the culture vessel without the use of a barrier membrane.

FIG. 4 is a plot comparing the outputs of a dissolved oxygen sensor positioned inside a culture vessel (internal sensor) and a dissolved oxygen sensor positioned outside the culture vessel (external sensor) without the use of a barrier membrane between the external sensor and the culture medium. The data shown in the plot of FIG. 4 is for gas phase measurements only.

The external sensor responds to the depleted oxygen in the flask, but it has a very long response time due to the diffusion kinetics of the culture vessel wall. As shown by the data from the internal sensor, the dissolved oxygen drops from approximately 90% to substantially 0% at approximately 14.3 hours. However, the signal from the external sensor drops of very slowly. At approximately 89 hours, the internal sensor measures an increase in the dissolved oxygen from approximately 0% to almost 100%. The signal from the external sensor, however, climbs very slowly.

Figure 5:
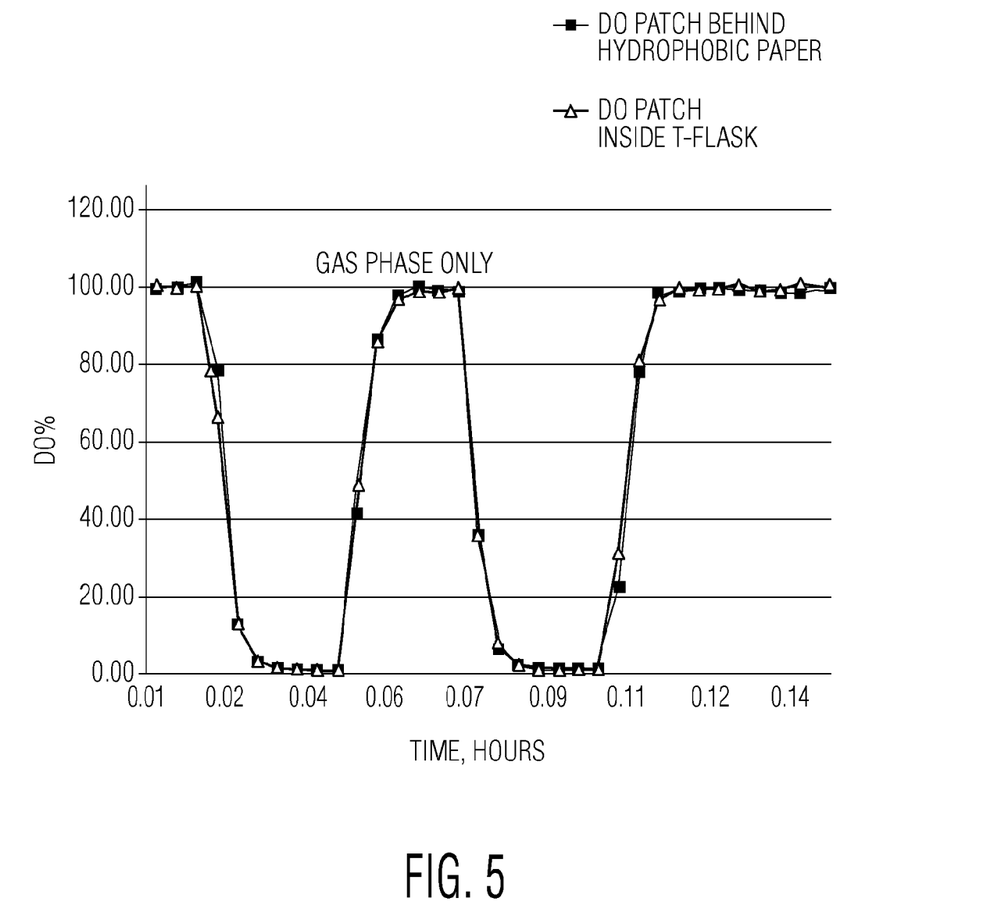
FIG. 5 is a plot comparing the outputs, for gas phase measurements, of a dissolved oxygen sensor positioned inside a culture vessel and a dissolved oxygen sensor positioned outside the culture vessel (external sensor) with a barrier membrane separating the external sensor from the growth medium.

FIG. 5 is a plot comparing the outputs, for gas phase measurements, of a dissolved oxygen sensor positioned inside a culture vessel (internal sensor) and a dissolved oxygen sensor positioned outside the culture vessel (external sensor) with a barrier membrane forming part of the culture vessel wall and separating the external sensor from the growth medium. As shown in FIG. 4, the measurements from the internal and external sensors track much more closely when a barrier membrane is used to separate the external sensor from the culture medium.

Figure 6:
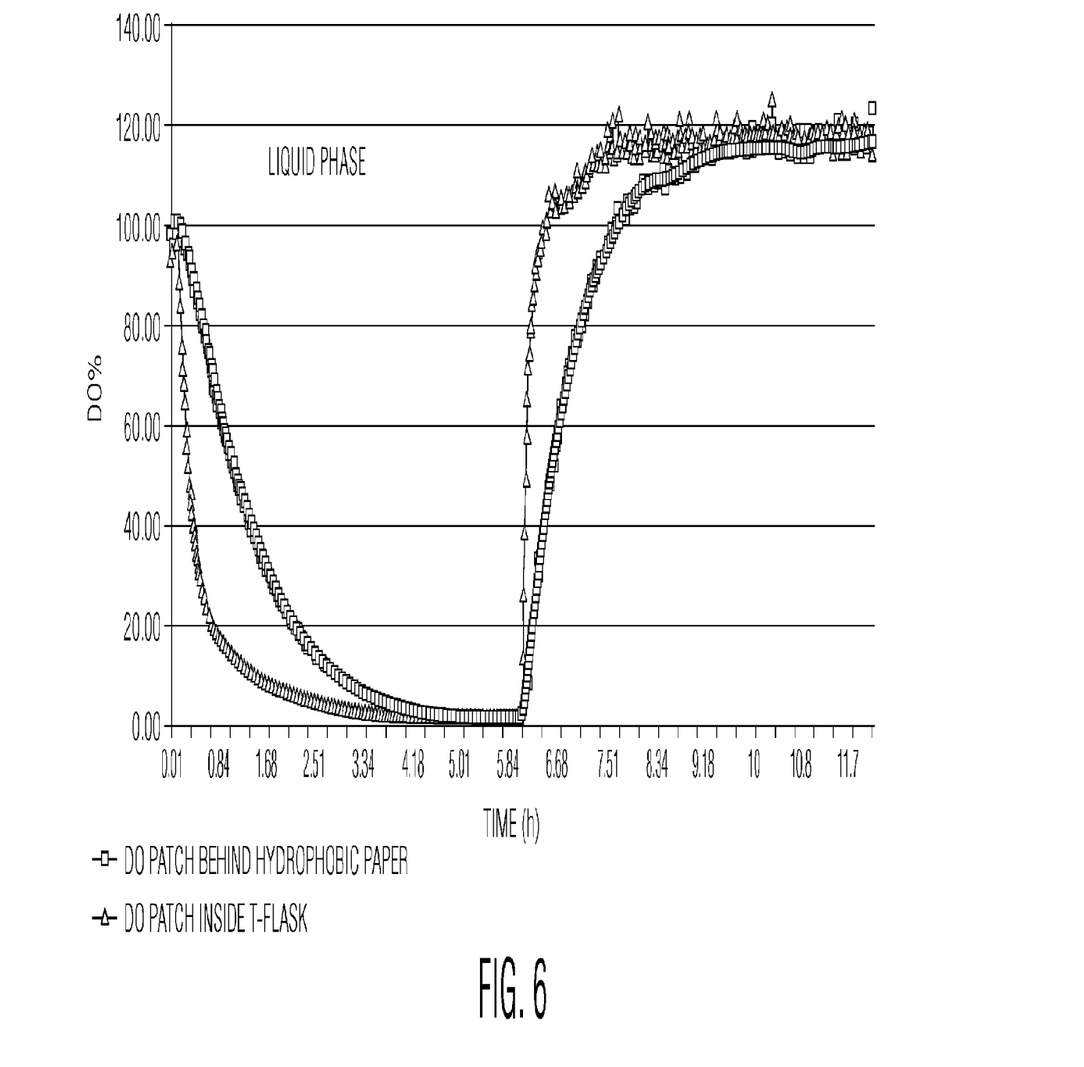
FIG. 6 is a plot comparing the outputs, for liquid phase measurements, of a dissolved oxygen sensor positioned inside a cuvette and a dissolved oxygen sensor positioned outside the cuvette (external sensor) with a barrier membrane separating the external sensor from the growth medium.

FIG. 6 is a plot comparing the outputs, for liquid phase measurements, of a dissolved oxygen sensor positioned inside a culture vessel (internal sensor) and a dissolved oxygen sensor positioned outside the culture vessel (external sensor) with a barrier membrane forming part of the culture vessel wall and separating the external sensor from the growth medium. As shown in FIG. 6, the liquid phase measurements show a greater deviation than the gas phase measurements shown in FIG. 5 due to the added mass transfer limitations of the barrier membrane and the thin film of stagnant liquid above the barrier membrane. However, this effect can be compensated for by adjusting the design of the physical layout, and by a different choice of membrane material.

Figure 7:
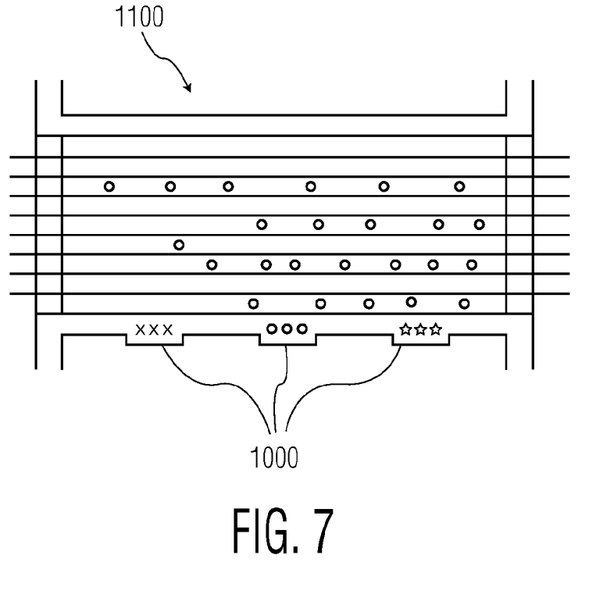
FIG. 7 is a schematic diagram of a hollow fiber or perfusion reactor 1100 that utilizes the non-invasive sensing systems 1000 of the present invention.
Figure 8:
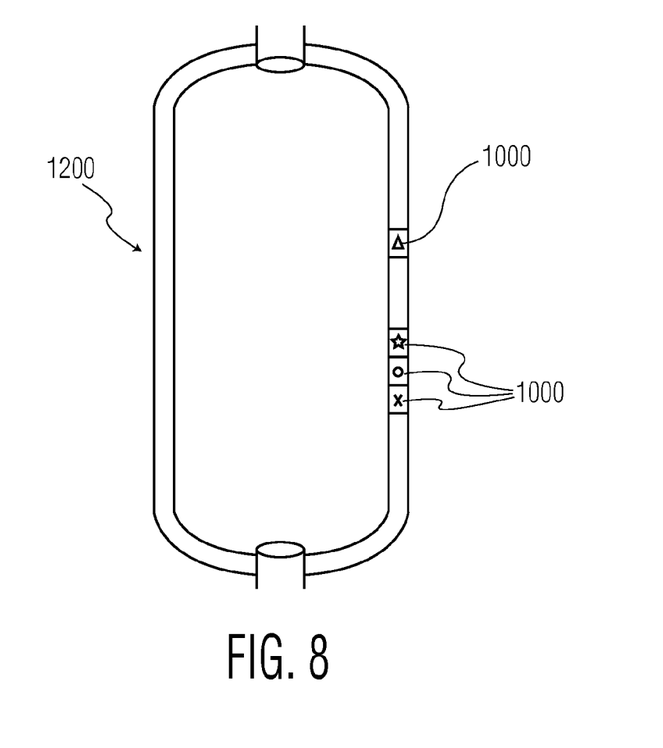
FIG. 8 is a schematic diagram of a chromatography column 1200 that utilizes the non-invasive sensing systems 1000 of the present invention.
Figure 9:
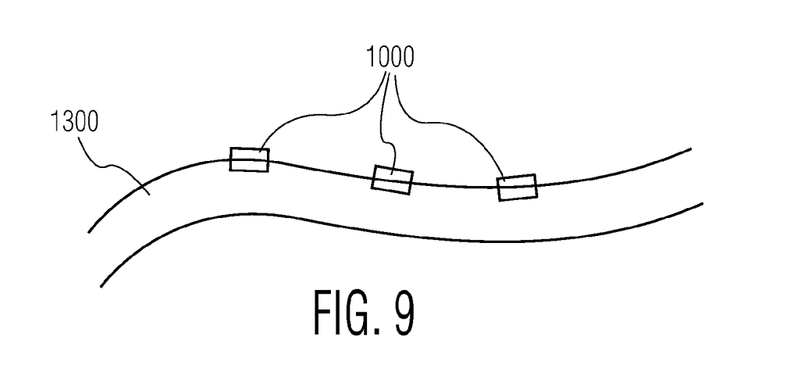
FIG. 9 is a schematic diagram of tubing 1300 that incorporates the non-invasive sensing systems 1000 of the present invention.
Figure 10:
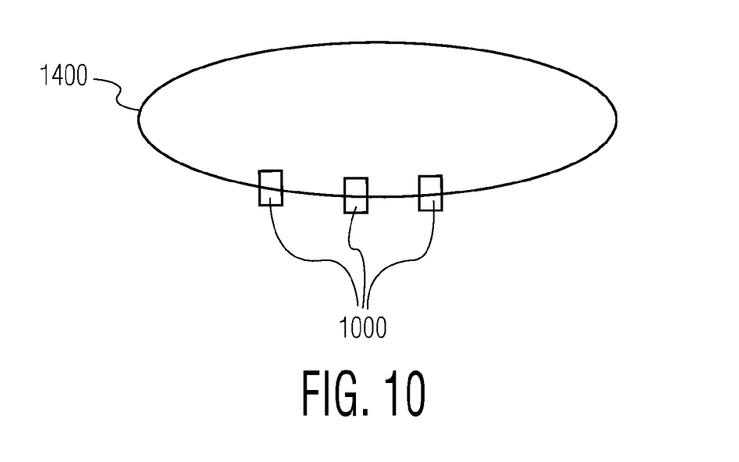
FIG. 10 is a schematic diagram of a bag 1400, such as a mixing, buffer or holding bag, that utilizes the non-invasive sensing systems 1000 of the present invention.
Figure 11:
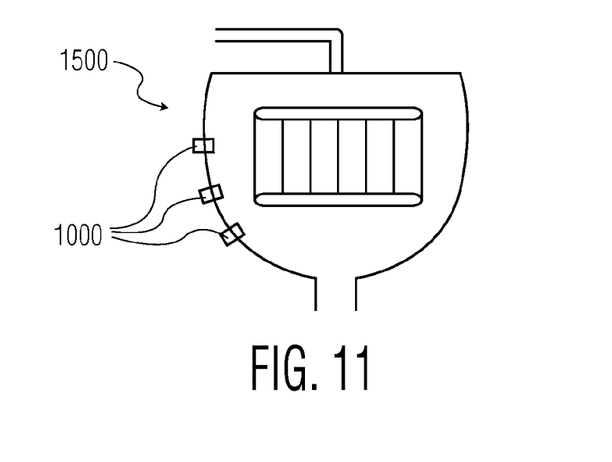
FIG. 11 is a schematic diagram of a membrane cartridge 1500 that utilizes the non-invasive sensing systems 1000 of the present invention.
Figure 12:
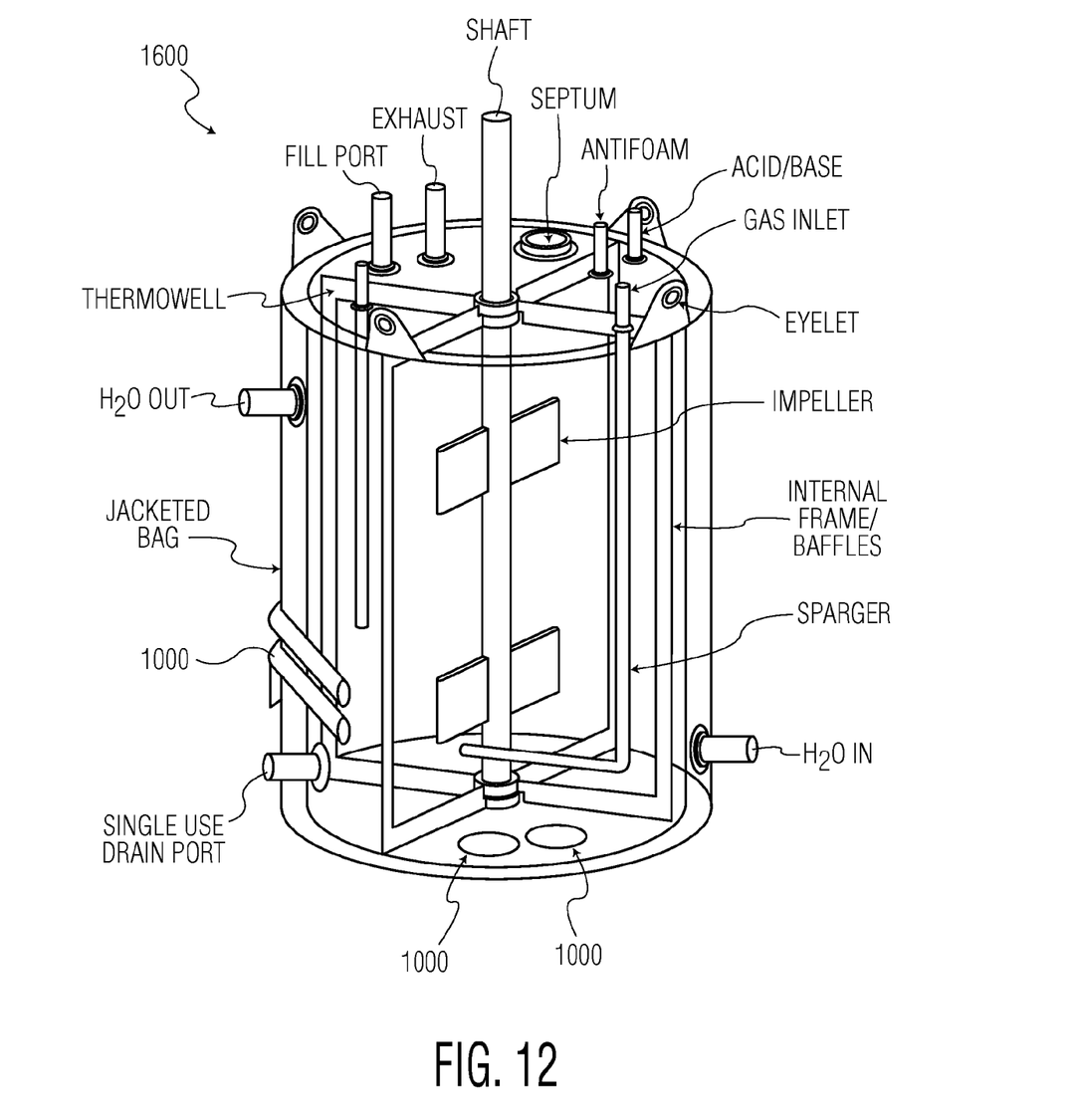
FIG. 12 is a schematic diagram of a disposable stirred tank bioreactor 1600 that utilizes the non-invasive sensing systems 1000 of the present invention.

FIGS. 7-12 show various process equipment examples in which the non-invasive sensing systems 1000 described above could be used as one or more sensor ports. FIG. 7 shows a hollow fiber or perfusion reactor 1100 that utilizes the non-invasive sensing systems 1000 of the present invention. FIG. 8 shows a chromatography column 1200 that utilizes the non-invasive sensing systems 1000 of the present invention. FIG. 9 shows tubing 1300 that incorporates the non-invasive sensing systems 1000 of the present invention. FIG. 10 shows a bag 1400, such as a mixing, buffer or holding bag, that utilizes the non-invasive sensing systems 1000 of the present invention. FIG. 11 shows a membrane cartridge 1500 that utilizes the non-invasive sensing systems 1000 of the present invention. FIG. 12 shows a disposable stirred tank bioreactor 1600 that utilizes the non-invasive sensing systems 1000 of the present invention.

The culture medium 30 employed in the non-invasive sensing systems 1000 described above will depend upon the particular cell type being cultivated and/or upon the concentration of analyte to be measured. Determining the appropriate culture medium is well within the purview of the skilled artisan. The culture parameters that can be measured with the present invention can include, but are not limited to, pH, dissolved oxygen (DO), carbon dioxide level, glucose concentration, phosphate concentration, ammonia concentration, lactate concentration, metal ion concentration, anion concentrations such as sulfate, nitrate, phosphate, additional nutrient concentrations including aminoacids and trace elements, flow rate, pressure, conductivity, protein product (including antibody) concentrations, proteins and DNA particularly in downstream processes etc.

The foregoing embodiments and advantages are merely exemplary, and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. Various changes may be made without departing from the spirit and scope of the invention, as defined in the following claims.

What is claimed is:

1. A plug-in sensor system for measuring at least one bioprocess parameter, comprising:
  a cartridge that is adapted to be selectively inserted into and removed from an opening in a wall of a culture vessel, wherein the cartridge comprises,
    a gas impermeable optically transparent layer;
    a sensor positioned on the optically transparent layer adapted to interact with an analyte being monitored, and
    a barrier membrane that is at least partially permeable to the analyte being monitored and that is positioned on and in contact with the sensor;
  wherein, when the cartridge is inserted into the opening in the wall of the culture vessel, the barrier membrane is positioned such that an analyte that is being monitored and that is present in the culture vessel must pass through the barrier membrane in order to come into contact with the sensor.

2. The system of claim 1, further comprising a hydrogel layer positioned between the barrier membrane and the sensor.

3. The system of claim 2, wherein the sensor comprises biosensors in a buffer solution.

* * * * *